(12) United States Patent
Laurell et al.

(10) Patent No.: US 7,700,134 B2
(45) Date of Patent: Apr. 20, 2010

(54) PREVENTION OF CISPLATIN INDUCED DEAFNESS

(75) Inventors: Goran Laurell, Stockholm (SE); Andreas Ekborn, Stockholm (SE); Josef Miller, Ann Arbor, MI (US); Hans Ehrsson, Stockholm (SE)

(73) Assignee: The Regents of the University of Michigan, Ann Arbor, MI (US)

( * ) Notice: Subject to any disclaimer, the term of this patent is extended or adjusted under 35 U.S.C. 154(b) by 1060 days.

(21) Appl. No.: 10/345,802

(22) Filed: Jan. 16, 2003

(65) Prior Publication Data

US 2003/0180388 A1 Sep. 25, 2003

Related U.S. Application Data

(60) Provisional application No. 60/349,801, filed on Jan. 17, 2002, provisional application No. 60/351,662, filed on Jan. 25, 2002.

(51) Int. Cl.
  *A61K 33/24* (2006.01)
  *A01N 47/28* (2006.01)
  *A61K 31/17* (2006.01)
(52) U.S. Cl. .................... 424/659; 514/580
(58) Field of Classification Search ............ 514/580, 514/581, 582, 589; 424/659
  See application file for complete search history.

(56) References Cited

U.S. PATENT DOCUMENTS 4,645,661 A 2/1987 Schonbaum
6,187,817 B1 * 2/2001 Campbell ............... 514/562

OTHER PUBLICATIONS

Church et al, (Hearing Research 86/1,2 (1995), 195-203).*
Brown (Hearing Research 70, 1993; 167-172).*
Lampers et al (Inorganic Chemistry, 1990, 29, 217-222).*
Registry No. 20537-886, ACS on STN 2006.*
Ishizawa et al. (Jpn J Pharmacology, Dec. 31, 1981, 6, 883-9, Abstract).*
Newmann et al. (J. of clinical Hematology and Oncology).*
van der Hulst et al., Annals of Otology, Rhinology & Laryngology 97:133 [1988].
Blakley et al., Archives of Otolaryngology Head & Neck Surgery 120:541 [1994].
Blakley et al., Otolaryngology Head & Neck Surgery 109:385 [1993].
Myers et al., Otolaryngology Head & Neck Surgery 104:122 [1991].
Nakai et al., Acta Oto Laryngologica 93:227 [1982].
Hensley et al., Journal of Clinical Oncology, 17:3333 [1999].
Camargo et al., Bio. Trace Elem. Res., 83:251 [2001].
Burchenal et al., Cancer Treatment Reports, 63:1493 [1979].
Ishizawa et al., Japanese Journal of Pharmacology 31:883 [1981].
Brown et al., Hear Res., 70:167 [1993].
Prieskorn and Miller, Hearing Res., 140:212 [2000].
Stover et al., Hear Res., 136:124 [1999].
Neary et al., Trends Neurosci 19:13 [1996].
Ryan, "Molecular study of hair celld evelopment and survival," Audio Neurootol 7:138-140 (2002).
Kingma et al., J. Neurosci. Methods 45:127 [1992].
Shoji et al., Hearing Res. 146:134 [2000].
Shoji et al., Hearing Res. 142:41 [2000].
Yamasoba et al., Brain Res. 815:317 [1999].
Lim et al, "Effects of cisplatin on the activities of reactive oxygen scavenging enzymes in rat kidney," K 'at' ollok Taehak Uihakpu Nonmunjip, 1993, vol. 46, No. 4, p. 1255-64.

* cited by examiner

*Primary Examiner*—Sreeni Padmanabhan
*Assistant Examiner*—Umamaheswari Ramachandran
(74) *Attorney, Agent, or Firm*—Casimir Jones, S.C.

(57) ABSTRACT

The present invention relates to compositions and methods for the protection and restoration of hearing. In particular, the present invention relates to methods and compositions for the prevention of chemical (e.g., cisplatin) induced deafness. The present invention thus provides methods of improving the outcome of subjects treated with cisplatin.

6 Claims, 2 Drawing Sheets

PREVENTION OF CISPLATIN INDUCED DEAFNESS

This application claims priority to U.S. provisional patent application Ser. No. 60/349,801, filed Jan. 17, 2002 and U.S. provisional patent application Ser. No. 60/351,662, filed Jan. 25, 2002.

This invention was made with government support under Grant No. DC04058 awarded by the National Institutes of Health. The Government has certain rights in the invention.

FIELD OF THE INVENTION

The present invention relates to compositions and methods for the protection and restoration of hearing. In particular, the present invention relates to methods and compositions for the prevention of chemical (e.g., cisplatin) induced deafness.

BACKGROUND OF THE INVENTION

Hearing impairment is the United State's number one disability. It has been estimated to compromise the quality of life and communication in more than 30 million Americans, and approximately 1 billion individuals worldwide. With the increase in longevity in life and the association of hearing impairment with aging, this disability is increasing in incidence and prevalence. In children, it severely affects education and future employment opportunities. In a working individual, it compromises the quality of life, job satisfaction, and productivity; and in the elderly, it leads to isolation and increased medical costs.

Sensorineural hearing loss is better known as nerve deafness. This is behind 95% of all hearing problems. It usually happens because the tiny, sound-transmitting structures deep within the ear wear down or get damaged. Sound enters the inner ear, but it doesn't get sent to the brain in the right way. Nerve deafness can be caused by loud noise, use of ear-damaging or ototoxic drugs, infections like measles and meningitis, an accident or trauma, or a birth or hereditary defect. Treatments for nerve deafness (e.g., hearing aids), allow for improved hearing and improved quality of life in some individuals.

The remaining 5% of hearing problems are due to conductive hearing loss. In these conditions, sound is not transferred from the outer to the inner ear. Conductive hearing loss can result from a punctured eardrum, severely impacted earwax (cerumen), head trauma, birth defects, or heredity. While currently available treatments are effective for certain types of hearing loss, additional treatments for the prevention of deafness remained needed.

SUMMARY OF THE INVENTION

The present invention relates to compositions and methods for the protection and restoration of hearing. In particular, the present invention relates to methods and compositions for the prevention of chemical (e.g., cisplatin) induced deafness.

Accordingly, in some embodiments, the present invention provides a method for reducing chemotherapy induced ototoxicity, comprising: providing a subject; a chemotherapeutic agent that induces ototoxicity; and an ototoxicity preventing agent; and administering the ototoxicity preventing agent locally to an ear of the subject; administering the chemotherapeutic agent to the subject. In some preferred embodiments, the chemotherapeutic agent is active in the presence of the ototoxicity preventing agent. In some embodiments, the chemotherapeutic agent is cisplatin. In some embodiments, the ototoxicity preventing agent is thiourea. In other embodiments, the ototoxicity preventing agent is dimethylthiourea. In some embodiments, the administering is via an osmotic pump implanted in the ear of the animal. In other embodiments, the administering is via manual injection into a cochleostomy. In still further embodiments, the administration is via diffusion from the middle ear. In some embodiments, the method further comprises the step of administering a nephrotoxicity preventing agent to the subject. In some embodiments, the nephrotoxicity agent is administered systemically. In some embodiments, the nephrotoxicity preventing agent includes, but it not limited to, sodium selenite and amifostine.

The present invention further provides a kit for use in preventing chemotherapy induced ototoxicity, comprising: a ototoxicity preventing agent; and instructions for using the kit for preventing chemotherapy induced ototoxicity. In some embodiments, the ototoxicity preventing agent is thiourea. In other embodiments, the ototoxicity preventing agent is dimethylthiourea. In some embodiments, the kit further comprises a local delivery system. In other embodiments, the kit further comprises an nephrotoxicity preventing agent. In some embodiments, the nephrotoxicity preventing agent includes, but it not limited to, sodium selenite and amifostine.

The present invention additionally provides a kit, comprising an ototoxicity preventing agent, wherein the ototoxicity preventing agent is formulated for local delivery; and a chemotherapeutic agent. In some embodiments, the chemotherapeutic agent is cisplatin. In some embodiments, the ototoxicity preventing agent is thiourea. In other embodiments, the ototoxicity preventing agent is dimethylthiourea. In some embodiments, the kit further comprises a local delivery system. In other embodiments, the kit further comprises an nephrotoxicity preventing agent. In some embodiments, the nephrotoxicity preventing agent includes, but it not limited to, sodium selenite and amifostine.

In yet other embodiments, the present invention provides a method for reducing chemotherapy induced ototoxicity, comprising: providing a subject; a chemotherapeutic agent that induces ototoxicity; and an ototoxicity preventing agent; and administering the ototoxicity preventing agent and the chemotherapeutic agent to the subject. In some preferred embodiments, the ototoxicity agent is administered prior to administering the chemotherapeutic agent. In some preferred embodiments, the ototoxicity preventing agent is administered locally to an ear of the subject. In some preferred embodiments, the chemotherapeutic agent is active in the presence of the ototoxicity preventing agent. In some embodiments, the chemotherapeutic agent is cisplatin. In some embodiments, the ototoxicity preventing agent is thiourea. In other embodiments, the ototoxicity preventing agent is dimethylthiourea. In some embodiments, the administering is via an osmotic pump implanted in the ear of the animal. In other embodiments, the administering is via manual injection into a cochleostomy. In still further embodiments, the administration is via diffusion from the middle ear. In some embodiments, the method further comprises the step of administering a nephrotoxicity preventing agent to the subject. In some embodiments, the nephrotoxicity agent is administered systemically. In some embodiments, the nephrotoxicity preventing agent includes, but it not limited to, sodium selenite and amifostine.

DESCRIPTION OF THE DRAWING

FIG. 1 shows the effect of thiourea treatment on cisplatin induced deafness.

DEFINITIONS

Figure 1A:
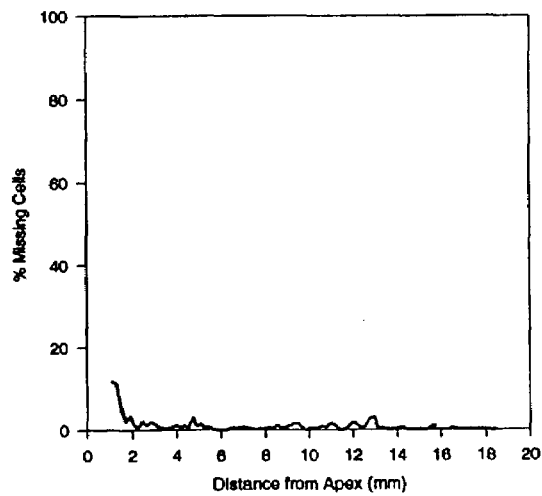
FIG. 1A shows outer hair cell loss vs. distance from apex.
Figure 1A:
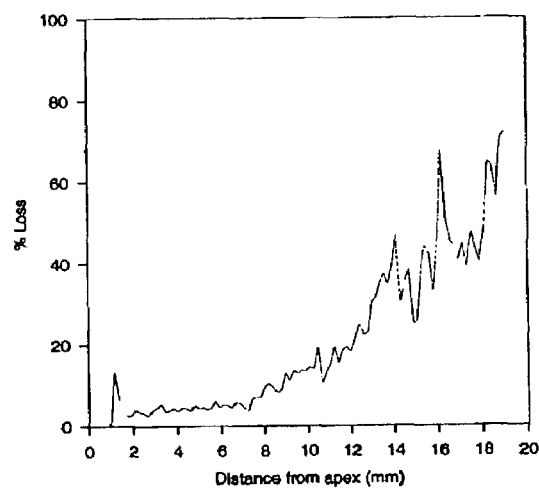
Figure 1A:
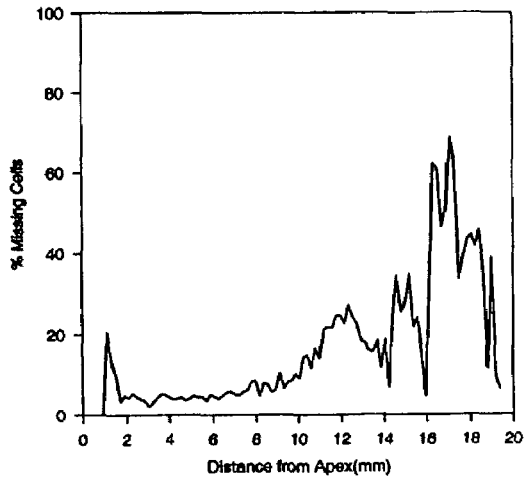
Figure 1A:
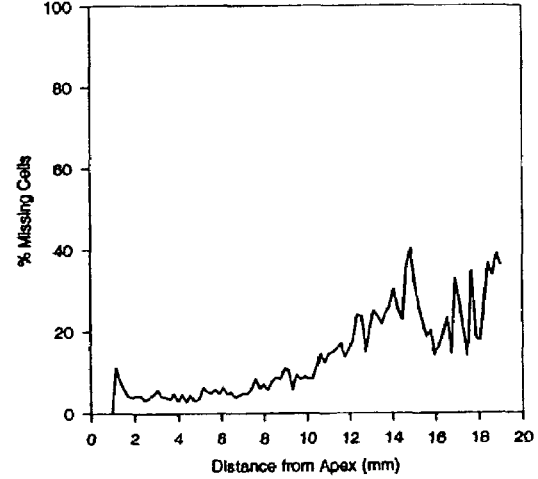

To facilitate an understanding of the present invention, a number of terms and phrases are defined below:

As used herein, the term "chemotherapeutic agent" when used in relation to cancer chemotherapy, refers to any agent that results in the death of cancer cells or inhibits the growth or spread of cancer cells. Examples of such chemotherapeutics include alkylating agents, antibiotics, antimetabolitic agents, plant-derived agents, and hormones. In some embodiments, the chemotherapeutic agent is cisplatin.

As used herein, the term "therapeutically effective amount" refers to an amount sufficient to reduce by at least about 15 percent, preferably by at least 50 percent, more preferably by at least 90 percent, and most preferably prevent, a clinically significant deficit in the activity, function, and/or response of a host. Alternatively, a therapeutically effective amount is sufficient to cause an improvement in a clinically significant condition in a host.

As used herein, the term "ototoxicity preventing agent" refers to any agent that reduces chemical induced ototoxicity (e.g., induced by a chemotherapeutic agent) by at least about 15 percent, preferably by at least 50 percent, more preferably by at least 90 percent, and most preferably at least 99 percent.

As used herein, the term "nephrotoxicity preventing agent" refers to any agent that reduces chemical induced nephrotoxicity (e.g., induced by a chemotherapeutic agent) by at least about 15 percent, preferably by at least 50 percent, more preferably by at least 90 percent, and most preferably at least 99 percent.

As used herein, the term "said chemotherapeutic agent is active in the presence of said ototoxicity preventing agent" refers to conditions where the chemotherapeutic activity (e.g., the ability to kill cancer cells) is not eliminated or substantially reduced (e.g., the chemotherapeutic agent remains active in the presence of the agent). The chemotherapeutic activity can be measured using any suitable method. For example, in some embodiments, the chemotherapeutic activity is measured by using animals comprising tumors known to be reactive to chemotherapeutic agents and comparing the ability of the agent to reduce tumor size in the presence and absence of the candidate ototoxicity-preventing agent.

As used herein, the term "local delivery" as in "local delivery" to the ear refers to the administration of a compound (e.g., an ototoxicity preventing agent of the present invention) in such a manner that the compound is present in the ear. In preferred embodiments, local delivery results in minimal, and preferably no detectable levels in the blood stream.

As used herein, the term "local delivery system" refers to a system for the local delivery of a compound (e.g., an ototoxicity preventing agent of the present invention). Local delivery systems include, but are not limited to, those disclosed herein (e.g., a mini-osmotic pump).

As used herein, the term "formulated for local delivery" as in a compound (e.g., an ototoxicity preventing agent of the present invention) formulated for local delivery refers to a formulation that is suitable for local delivery to the ear (e.g., using a local delivery system).

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk$^-$ cell lines, the CAD gene that is used in conjunction with CAD-deficient cells and the mammalian hypoxanthine-guanine phosphoribosyl transferase (hprt) gene that is used in conjunction with hprt$^-$ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to compositions and methods for the protection and restoration of hearing. In particular, the present invention relates to methods and compositions for the prevention of cisplatin-induced deafness.

Cisplatin is an anti-cancer agent that is used in the treatment of a variety of solid tumors. In adults, indications for cisplatin include the treatment of primary germ cell tumors, as well as metastatic tumors from the testis and ovary. In children, cisplatin-based chemotherapy is used for osteogenic sarcoma and Ewing's sarcoma. While an effective chemotherapeutic, cisplatin unfortunately has profound toxicity that severely limits its clinical application. In particular, cisplatin is known to cause kidney damage, peripheral neuropathy, and hearing loss.

Cisplatin-induced hearing loss typically affects the high-frequency range, although some patients develop a social hearing handicap as the hearing loss extends to lower frequencies during subsequent treatment courses (van der Hulst et al., Annals of Otology, Rhinology & Laryngology 97:133 [1988]). Risk factors for cisplatin-induced hearing loss include anemia and hypoproteinemia (Blakley et al., Archives of Otolaryngology—Head & Neck Surgery 120:541 [1994]). While not strictly stereo-typed across patients, cisplatin-induced hearing loss, the reported incidence of which varies from 9-90%, is typically cumulative and non-reversible (Blakley et al., Otolaryngology—Head & Neck Surgery 109: 385 [1993]). Severe impairment can occur early in the course of treatment, without a clear correlation with cumulative dose (Myers et al., Otolaryngology—Head & Neck Surgery 104: 122 [1991]). In animal models, anatomical changes observed with cisplatin include preferential loss of outer hair cells with preservation of inner hair cells; damage is greatest in the base of the cochlea, as expected given the high-frequency nature of the associated hearing loss (Nakai et al., Acta Oto-Laryngologica 93:227 [1982]).

Nephrotoxicity, which occurs in a dose-related fashion, has long been considered to be the primary limiting toxicity of cisplatin. The risk of nephrotoxicity can be minimized by dose reduction, use of alternative agents (e.g., carboplatin), and co-administration of amifostine or sodium selenite (Hensley et al., Journal of Clinical Oncology, 17:3333 [1999]; Camargo et al., Bio. Trace Elem. Res., 83:251 [2001]). In contrast, amifostine does not appear to be effective in ameliorating neuropathic and ototoxic effects of cisplatin (Hensley et al., Journal of Clinical Oncology, 17:3333 [1999]). With improved prevention of nephrotoxicity, ototoxicity is now considered to be the primary limiting factor on the use of cisplatin clinically.

Accordingly, the present invention provides methods and compositions for preventing cisplatin-induced ototoxicity. The methods of the present invention thus allow for cisplatin to be used much more effectively as a cancer-treating agent.

I. Protective Compounds

In some embodiments, small, neutral molecules are utilized as protective agents against cisplatin. In some preferred embodiments the molecules are strong nucleophiles. In some preferred embodiments, small, neutral and highly potent molecules that can reach inner ear targets when administered in the middle ear are utilized. For example, in some embodiments, thiourea is utilized.

In other embodiments, dimethyl-thiourea is utilized as a protective agent. The present invention is not limited to a particular agent. Any agent that is protective against the effects of cisplatin without interfering with cisplatin when administered locally may be utilized in the methods and compositions of the present invention. For example, a variety of thiourea-like compounds are contemplated. Compounds may be screened using any suitable assay including, but not limited to, the assay described in the illustrative example below.

In preferred embodiments, the protective agents of the present invention are formulated for local delivery. Techniques for formulation and administration may be found in the latest edition of "Remington's Pharmaceutical Sciences" (Mack Publishing Co, Easton Pa.). As is well known in the medical arts, dosages for any one patient depends upon many factors, including the patient's size, body surface area, age, the particular compound to be administered, sex, time and route of administration, general health, and interaction with other drugs being concurrently administered.

II. Administration of Treatments

When given systemically, thiourea eliminates the therapeutic efficacy of cisplatin (Burchenal et al., Cancer Treatment Reports, 63:1493 [1979]; Ishizawa et al., Japanese Journal of Pharmacology 31:883 [1981]). Consequently, it is preferred that this agent be used with cisplatin in a systemic manner as a rescue strategy. However, the small size of thiourea makes it amenable to the direct, local delivery methods of present invention, which allow delivery into the inner ear, thereby allowing the drug to prevent cisplatin-induced deafness while not interfering with the anti-tumor effects of cisplatin.

Accordingly, in preferred embodiments, protective compounds are administered directly to the ear. In preferred embodiments, systemic levels of the protective compound are low, so as not to interfere with the chemotherapeutic agent. Experiments conducted during the course of the development of the present invention (Illustrative Example below) demonstrated that administration of thiourea via a mini-osmotic pump prevented cisplatin-induced ototoxicity. Thus, in some embodiments, protective agents are administered via a mini-osmotic pump (Brown et al., Hear Res., 70:167 [1993]; Prieskorn and Miller, Hearing Res., 140:212 [2000]). In some embodiments, a cannula system is utilized to provide access, via a hand-drilled cochleostomy, to the inner ear, while allowing periodic pump changes in order to enable changes in the drug being infused over time, and/or to prolong the interval of drug delivery. In some embodiments, the cannula allows direct (manual) injection into the cochlea, as accessed through the round window or via a cochleostomy (Stover et al., Hear Res., 136:124 [1999]), as well as round window placement of the cannula tip for the purposes of middle ear drug delivery.

In other embodiments, treatments are injected into the cochlea through a cochleostomy created in the basal turn via manual injection (Brown et al., Hear Res., 70:167 [1993]; Prieskorn and Miller Hear Res., 140:212 [2000]). In still further embodiments, treatments are administered via indirect infusion. This method takes advantage of the semi-permeable nature of the round window membrane to deliver small molecules into the middle ear space, from which they pass into the inner ear. In yet other embodiments, the treatment is incorporated into a biopolymer matrix on a cochlear implant, resulting in gradual, chronic release of the substance from along the implant's length within the cochlea. The present invention is not limited to the local delivery methods described herein. Any suitable method that delivers therapeutics to the inner ear may be utilized.

III. Kits

In some embodiments, the present invention provides kits comprising the ototoxicity preventing agents of the present invention (e.g., thiourea). In some preferred embodiments, the ototoxicity preventing agent (e.g., thiourea) is supplied as a formulation suitable for local delivery. In some embodiments, the kits comprise instructions for the use and administration of the agents. In some embodiments, the kits comprise both the protective agent (e.g., thiourea) and the chemotherapeutic agent (e.g., cisplatin).

Experimental

The following example is provided in order to demonstrate and further illustrate certain preferred embodiments and aspects of the present invention and is not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); and ° C. (degrees Centigrade).

Intracochlear Administration of Thiourea Protects Against Cisplatin Induced Ototoxicity in the Guinea Pig This example describes the protective effect of thiourea when administered intracochlearly. 20 pigmented guinea pigs were used. The procedure was as follows:

1) Pre-treatment otoscopy and ABR assessment of left ear to assure normal ear status.

2) Surgical implant of a cannula into the perilymphatic space of the left cochlea, connected to osmotic pump (Alzet 0.5 μL/hour, 14 days) filled with artificial perilymph (AP) (n=10) or thiourea 27 mg/mL (n=10), followed by 3 day recovery.

3) Repeated otoscopy and ABR threshold assessment to assure normal inner ear status after implant.

4) Animals administered 8 mg/b.w. cisplatin (IV) and 15 ml saline (SQ), for nephroprotection.

5) Five days after cisplatin treatment animals were anesthetized, ABR's assessed, cannula position and middle ear normality confirmed, sacrificed and surface preparations prepared for hair cell assessment.

Figure 1B:
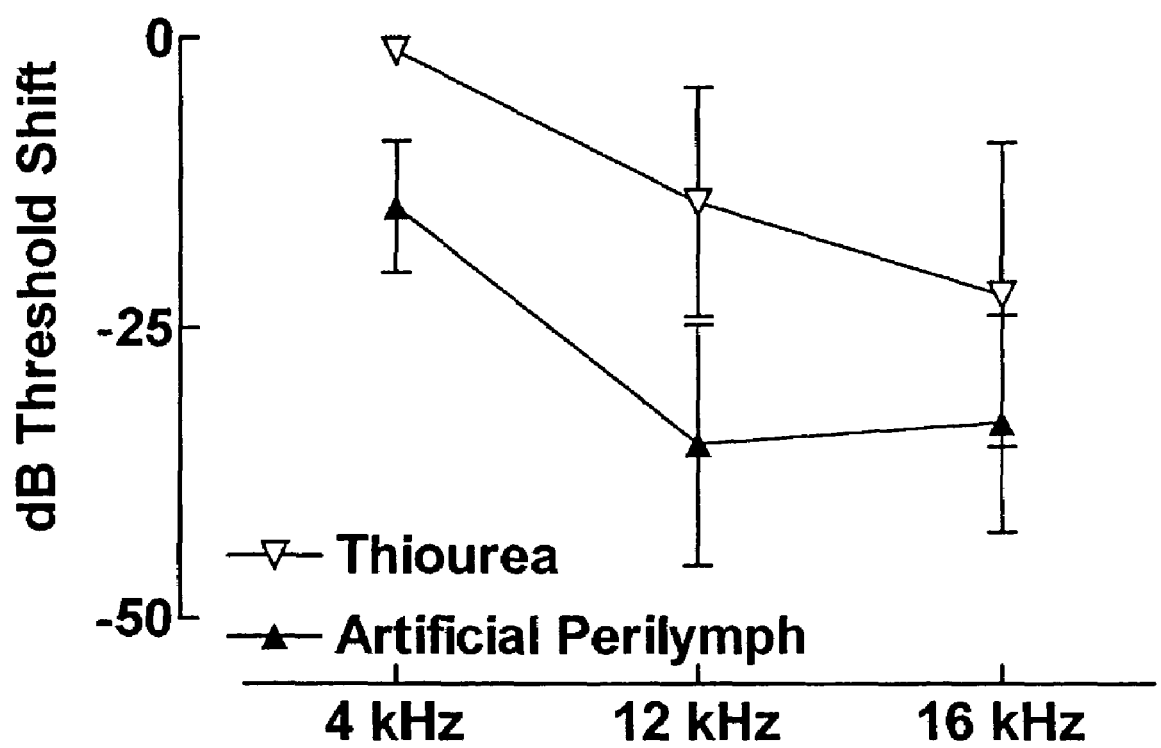
FIG. 1B shows dB threshold shift.

Of the ten guinea pigs in each group, 8 (AP) and 5 (thiourea) animals were evaluated. Seven animals were excluded because of surgical complications, other middle ear afflictions or general health. The results are shown in FIG. 1. FIG. 1A shows the % loss. The 2 top panels represent thiourea treated animals. The 2 panels on the left represent treated ears, the 2 on the right represent untreated ears. Thiourea treated ears demonstrated significantly (p<0.05) lower OHC loss compared to the untreated, right ears and significantly (p<0.05) less OHC loss compared to the AP treated ears. There was no difference between left and right ears in the AP treated animals and no difference between untreated ears in the thiourea and AP groups. FIG. 1B shows the average threshold shift for both groups. The average threshold shift did not differ between the groups. Thus, this example demonstrates that thiourea offers protection from cisplatin induced ototoxicity.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method for reducing chemotherapy induced ototoxicity, comprising:
 a) providing
  i) a subject in need of chemotherapy,
  ii) a chemotherapeutic agent that induces ototoxicity, wherein said chemotherapeutic agent is cisplatin; and
  iii) an ototoxicity preventing agent wherein said agent is thiourea or dimethylthiourea; and
 b) administering a therapeutically effective amount of said ototoxicity preventing agent locally to an inner ear of said subject via a pump, wherein said administration of said ototoxicity preventing agent reduces ototoxicity in said subject when compared to ototoxicity present in said subject if said ototoxicity preventing agent was not administered;
 c) administering said chemotherapeutic agent to said subject.

2. The method of claim 1, wherein said chemotherapeutic agent is active in the presence of said ototoxicity preventing agent.

3. The method of claim 1, wherein said pump is an osmotic pump.

4. The method of claim 1, further comprising the step of administering a nephrotoxicity preventing agent to said subject.

5. The method of claim 4, wherein said nephrotoxicity preventing agent is selected from the group consisting of sodium selenite and amifostine.

6. The method of claim 1, wherein said pump is implanted in said ear of said animal.

* * * * *